US011305459B2

(12) United States Patent
Bollin

(10) Patent No.: US 11,305,459 B2
(45) Date of Patent: Apr. 19, 2022

(54) DEVICE AND METHOD FOR SEMI-AUTOMATIC CONCRETE MIXING AND FOR TRAINING OPERATORS FOR USE THEREOF

(71) Applicant: Neil Edward Bollin, Checotah, OK (US)

(72) Inventor: Neil Edward Bollin, Checotah, OK (US)

( * ) Notice: Subject to any disclaimer, the term of this patent is extended or adjusted under 35 U.S.C. 154(b) by 0 days.

(21) Appl. No.: 16/804,634

(22) Filed: Feb. 28, 2020

(65) Prior Publication Data

US 2021/0178632 A1 Jun. 17, 2021

Related U.S. Application Data

(60) Provisional application No. 62/948,294, filed on Dec. 15, 2019.

(51) Int. Cl.
*B28C 7/02* (2006.01)
*B28C 9/00* (2006.01)
*B28C 7/12* (2006.01)

(52) U.S. Cl.
CPC .............. *B28C 7/024* (2013.01); *B28C 7/12* (2013.01); *B28C 9/002* (2013.01)

(58) Field of Classification Search
CPC .................................................... B28C 7/024
USPC ...................................................... 366/8, 17
See application file for complete search history.

(56) References Cited

U.S. PATENT DOCUMENTS

| | | |
|---|---|---|
| 1,328,765 A | 1/1920 | Robb |
| 1,410,126 A | 3/1922 | Rosendahl |
| 1,781,549 A | 3/1929 | Johnson |
| 2,273,750 A | 11/1936 | Clagett, Jr. |
| 2,342,749 A | 8/1941 | Maxon, Jr. |
| 2,543,883 A | 9/1945 | Von Saspe |
| 3,160,393 A | 12/1964 | Councilman |
| 3,237,437 A | 3/1966 | Hilkemeier |
| 3,463,462 A | 8/1969 | Sarff et al. |
| 3,731,909 A | 5/1973 | Johnson |
| 3,767,170 A | 10/1973 | Morgenstern |
| 3,924,447 A | 12/1975 | Garrison |
| 4,008,093 A | 2/1977 | Kitsuda et al. |
| 4,318,177 A | 3/1982 | Rapp et al. |
| 4,356,723 A | 11/1982 | Fay |
| 4,544,275 A | 10/1985 | Hudelmaier |
| 4,899,154 A | 2/1990 | Waitzinger et al. |
| 5,352,035 A | 10/1994 | Macaulay et al. |
| 5,527,387 A | 6/1996 | Anderson et al. |
| 5,713,663 A * | 2/1998 | Zandberg .............. B28C 7/0454 366/8 |
| 7,320,539 B2 | 1/2008 | Christenson et al. |
| 8,020,431 B2 * | 9/2011 | Cooley ................... B28C 5/422 73/54.03 |
| 8,118,473 B2 * | 2/2012 | Compton ................ B28C 5/422 366/17 |
| 8,727,604 B2 | 5/2014 | Compton et al. |
| 8,746,954 B2 | 6/2014 | Cooley et al. |
| 8,764,272 B2 | 7/2014 | Hazrati et al. |
| 8,764,273 B2 | 7/2014 | Koehler et al. |
| 8,858,061 B2 * | 10/2014 | Berman .................... B28C 7/02 366/10 |
| 9,506,785 B2 | 11/2016 | Turk |
| 11,092,528 B2 | 8/2021 | Bollin |
| 2007/0263478 A1 | 11/2007 | Burch |
| 2011/0077778 A1 * | 3/2011 | Berman ................. G05B 15/02 700/265 |
| 2013/0021867 A1 | 1/2013 | Shimizu |

FOREIGN PATENT DOCUMENTS

| | | |
|---|---|---|
| CA | 2246191 | 3/1999 |
| CA | 2503779 | 7/2005 |
| EP | 0126573 A1 | 11/1984 |
| WO | 2010110814 A1 | 9/2010 |
| WO | 2010111204 A1 | 9/2019 |

OTHER PUBLICATIONS

Concrete Controls; "Continuous automatic slump control . . . right to the pour." Retrieved on Nov. 21, 2019 from http://concretecontrols.com/DHSpage.html.
Concrete Controls; "Continuous slump control right to the Pour. Guaranteed!"; Hydraslump; Retrieved Nov. 21, 2019 from http://concretecontrols.com/DHSpage.html.
Concrete Controls; "Installation instructions for Dial-a-Matic & Semi-matic Hydra-slump Technical Information Sheet, DHS-94"; Retrieved on Nov. 21, 2019 from http://concretecontrols.com/DHSpage.html.
Environmental Expert; "Seale-Tron Inc. BatchTron—Model I—Little Batch Controller"; retrieved on Nov. 21, 2019 from https://www.environment-expert.com.
Gaynor, Richard D.; "Understanding ASTM C94"; Copyright 1996.
Texas DOT; "Section 3: Concrete Plant Operation"; retrieved on Jan. 23, 2020 from http://onlinemanuals.txdot.gov/txdotmanuals/pdm/conc_plant_operation.htm.

(Continued)

Primary Examiner — David L Sorkin
(74) Attorney, Agent, or Firm — Robert H. Frantz

(57) ABSTRACT

A system and method for automatically controlling concrete batch mixing cycles and for training an operator to minimize the mixing cycles, includes receiving real time mixer motor power measurements; detecting an initial peak value among the real time mixer motor power measurements; determining, by a processor, an initial amount of water to add to a concrete batch; waiting a first time period to determine a first supplemental amount of water to add to a concrete batch; and, then, periodically determining additional supplemental amounts of water to add to a concrete batch; until, the real time mixer motor power measurements meet a pre-determined target mixer motor power value, responsive to which, one or more outputs are activated, such as a user interface indicator that the batch is ready, or an optional electronic signal to a batch control system to dump the batch, or both.

9 Claims, 15 Drawing Sheets

(56) References Cited

OTHER PUBLICATIONS

CE-REF; Concrete Construction: ASTM C-94 Standard Specification for Ready-Mixed Concrete; retrieved on Ja. 23, 2020 from http://www.ce-ref.com/Construction/Ready_concrete/ASTM_C94.html.
Scaletron; "Concrete Batch Controls"; retrieved on Jan. 23, 2020 from https://scaletron.com.
Dougherty, William; "Ready-Mix Concrete"; retrieved on Jan. 23, 2020 from https://www.engr.psu.edu/ce/courses/ce584/concrete/library/construction/.
Cazacliu et al.; "New methods for accurate water dosage in concrete central mix plants"; Jan. 2008, from ResearchGate.
Mixer Drivers Forum; "How to read a slump gauge?"; Apr. 16, 2008, at https://compcorner.proboards.com.
MP Parts; "CBMW 80200624 Slump Meter Gauge—5000 PSI", retrieved from https://mpparts.com on Jan. 6, 2022.
Wikipedia; "Concrete slump test"; retrieved from https://en.wikipedia.org on Jan. 7, 2022.
MP Parts; "Terex 34656 Electric Slump Meter Gauge MY14", retrieved from https://mpparts.com on Jan. 6, 2022.

\* cited by examiner

600

ULTAMETER (HMI WebServer) - VNC Viewer

| No. | Date | Time | ST-Delay | Batch | Feed | Mix | Dump | Peak | Final | Temp |
|---|---|---|---|---|---|---|---|---|---|---|
| 29 | 01/09/20 | 17:20:40 | 27 | 47 | 32 | 0 | 15 | 362 | 362 | 0 |
| 28 | 01/09/20 | 17:19:25 | 9 | 58 | 19 | 27 | 12 | 362 | 362 | 0 |
| 27 | 01/09/20 | 17:18:23 | 34 | 47 | 33 | 0 | 14 | 362 | 362 | 0 |
| 26 | 01/09/20 | 17:16:57 | 49 | 95 | 88 | 0 | 13 | 354 | 354 | 33 |
| 25 | 01/09/20 | 17:15:28 | 787 | xxx | 50 | 0 | 14 | 357 | 357 | 65 |
| 24 | 01/09/20 | 16:57:12 | 55 | 101 | 50 | 39 | 12 | 337 | 337 | 0 |
| 23 | 01/09/20 | 16:55:23 | 28 | 17 | 4 | 0 | 13 | 362 | 362 | 0 |
| 22 | 01/09/20 | 16:54:03 | 11 | 17 | 4 | 0 | 13 | 192 | 192 | 32 |
| 21 | 01/09/20 | 16:52:57 | 33 | 48 | 32 | 0 | 16 | 329 | 329 | 57 |
| 20 | 01/09/20 | 16:51:43 | 123 | 88 | 71 | 0 | 18 | 277 | 277 | 58 |
| 19 | 01/09/20 | 16:48:26 | 34 | 129 | 89 | 27 | 13 | 422 | 422 | 98 |
| 18 | 01/09/20 | 16:46:04 | 1 | 199 | 186 | 0 | 13 | 363 | 296 | 175 |
| 17 | 01/09/20 | 16:42:56 | 40 | 69 | 54 | 0 | 15 | 431 | 431 | 41 |
| 16 | 01/09/20 | 16:41:18 | 8 | 54 | 20 | 23 | 11 | 364 | 364 | 0 |
| 15 | 01/09/20 | 16:40:29 | 3 | 118 | 90 | 17 | 11 | 364 | 364 | 0 |
| 14 | 01/09/20 | 16:30:10 | 28 | 32 | 17 | 0 | 15 | 206 | 206 | 0 |

© 2020 Neil Bollin

Menu Task

DEVICE AND METHOD FOR SEMI-AUTOMATIC CONCRETE MIXING AND FOR TRAINING OPERATORS FOR USE THEREOF

INCORPORATION BY REFERENCE

U.S. provisional patent application 62/948,294, filed on Dec. 15, 2019, by Neil Bollin, is incorporated by reference, in its entirety.

FIELD OF THE INVENTION

Authorization per 37 CFR 1.71(e):
"A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever."
The present patent application is a continuation-in-part of, and claims priority to, U.S. provisional patent application 62/948,294, filed on Dec. 15, 2019, by Neil Bollin. The invention generally relates to processes, devices and systems for timely completion of mixing of a batch of concrete according to a target slump or workability criteria.

BACKGROUND OF THE INVENTION

Concrete mixing systems are widely used in construction of buildings, roads, bridges, dams, and the like. Most central mixing plants comprise aggregate storage, cement/pozzolan storage, batchers, dust collectors, a mixer, and a feed system to carry the batched aggregate, cement, admixture and water to the mixer. "Batching" usually includes dispensing from associated storage batches of aggregate, cement/pozzolan, admixture, and water into the feed system, from which it is received into the mixture, where it is combined and mixed until ready to dump into a truck for delivery to the construction site. Batching can be done by weight or by volume, with weight being the more common method of batching. Most central mixing plants are designed and operated according to a standard such as ASTM C-94.

Slump, also referred to as workability, refers to the amount of deformation a certain prescribed amount and shape of concrete will exhibit when the form is removed while the concrete is still fresh and workable, before it is set or hardened. In the United States, there are at least two open standards from ASTM International (formerly known as American Society for Testing and Materials) and the American Association of State Highway and Transportation Officials (AASHTO) for the tools, fixtures, and processes for performing a slump test on fresh concrete. Additionally, some building codes provide various slump testing procedures, as well. Slump is one of several criteria commonly used to determine if a particular load of concrete is suitable to be used in the particular construction installation underway.

SUMMARY OF THE DISCLOSED EMBODIMENT(S)

Disclosed are example embodiments of a system and method for automatically controlling concrete batch mixing cycles and for training an operator to minimize the mixing cycles, includes receiving real time mixer motor power measurements; detecting an initial peak value among the real time mixer motor power measurements; determining, by a processor, an initial amount of water to add to a concrete batch; waiting a first time period to determine a first supplemental amount of water to add to a concrete batch; and, then, periodically determining additional supplemental amounts of water to add to a concrete batch; until, the real time mixer motor power measurements meet a pre-determined target mixer motor power value, responsive to which, one or more outputs are activated, such as a user interface indicator that the batch is ready, an optional electronic signal to a batch control system to dump the batch, or both.

BRIEF DESCRIPTION OF THE DRAWINGS

The description of exemplary embodiments of the invention as set forth herein are illustrated by the drawings.

FIG. 6 illustrates an example user interface for reviewing and adjusting mixer data according to at least one embodiment of the present invention.

FIG. 7 illustrates an example user interface for reviewing and adjusting feed data according to at least one embodiment of the present invention.

FIG. 10 illustrates an example user interface for reviewing and adjusting a data log for slump and load size according to at least one embodiment of the present invention.

DETAILED DESCRIPTION OF ONE OR MORE EXEMPLARY EMBODIMENT(S) OF THE INVENTION

Figure 1:
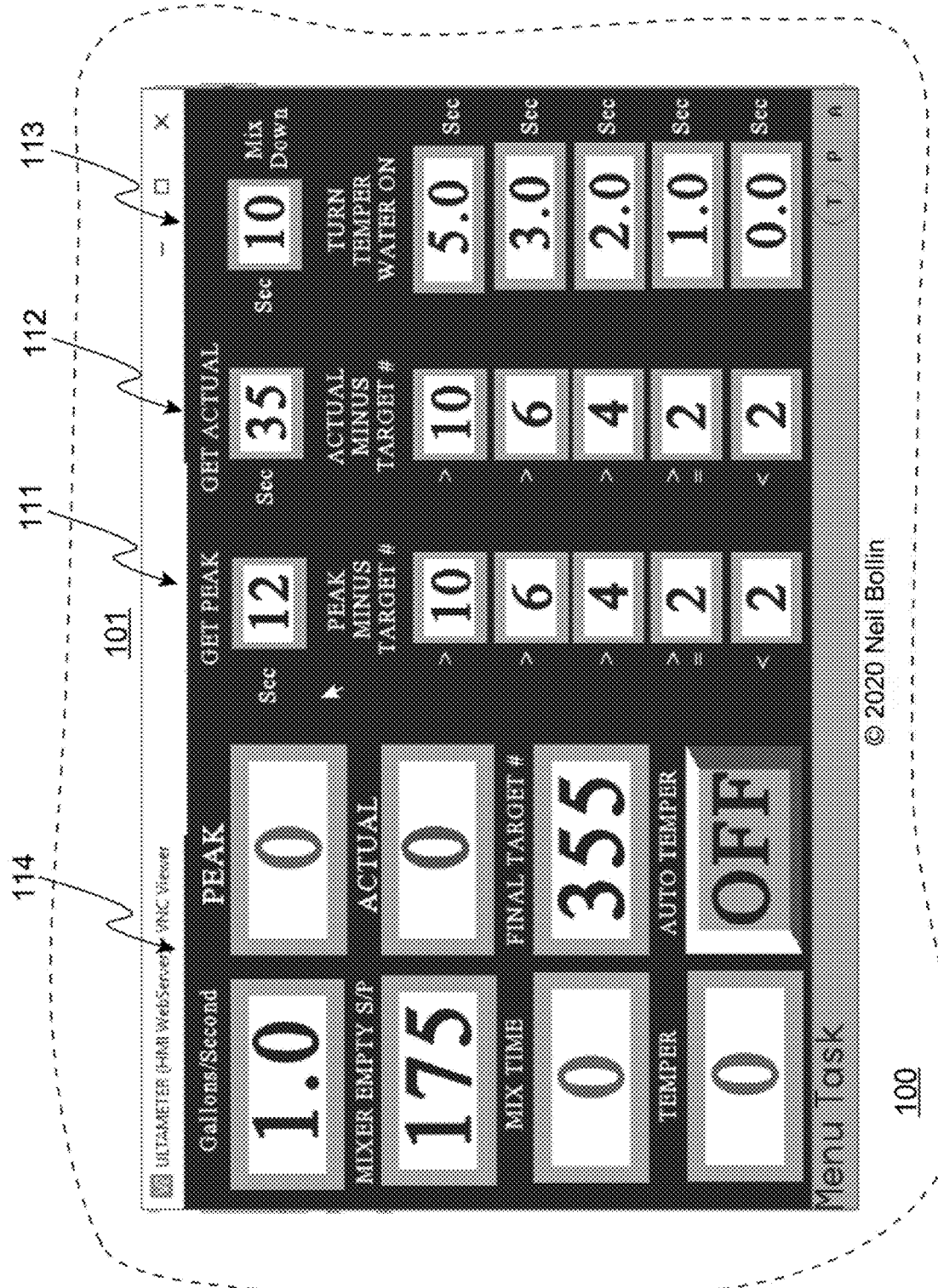
FIG. 1 illustrates an example user interface for adjusting settings to an automatic water program according to at least one embodiment of the present invention.

There are generally two production environments in which concrete is mixed:

(1) a "central-mix" operation which is a stationary concrete batching plant with a stationary mixer as part of the batching plant, and typically the mixer unit is electrically driven; and (2) a "ready-mix" operation which is a stationary concrete batching plant with mobile mixers where the mixers are usually truck-mounted and are separate from the rest of the batching plant, and typically the mixer unit is hydraulically driven.

Most of concrete production environments also include a mixer power sensor, such as a hydraulic pressure meter on a ready-mix mixer, or an electric amperage meter (or wattmeter) on a central-mix mixer, that measures the amount of energy (or work) required to turn the mixer's mixing drum, which is roughly correlated to an expected slump value of the concrete load being mixed therein.

The inventor of the present invention has recognized a problem in the art not previously recognized or addressed by existing mix automation systems providers: currently available batching systems and mixer operations do not emphasize the importance of the mixing process of the freshly mixed concrete, especially the cycle times and consistency required to be complete and ready to dump out of the mixer unit.

The human operators who are responsible for making the final decision as to when mixing is complete in the mixer often leave a batch of concrete in the mixer much longer than necessary, and far beyond the time in which the batch is truly ready to be dumped out of the mixer unit. This means that the next batch is delayed in being started, with the extended mix times and delays accumulating throughout the production day across the many batches of concrete that are mixed in the mixer unit. This reduces the productivity of the mixing operation without any increase in quality of the product.

Part of this problem was addressed in the incorporated patent disclosure regarding a slump meter, as operators of both central-mix and ready-mix systems rely on the slump meter to determine when a batch of concrete is ready to be discharged. While existing slump meters provide for an approximate prediction of the slump of the concrete load at a given time, their accuracy and dependability (repeatability) are seriously lacking, so the advanced slump meter described in the incorporated patent application is preferably utilized in some embodiments of the present invention, albeit hydraulic pressure is measured typically in the ready-mix operations and electrical amperage is measured typically in the central-mix systems.

Due to the practical inability of a concrete producer, using presently available technology, to actually produce concrete at precise slump (workability) that is required for consistency, strength and durability for a specified project, a slump or workability tolerance is permitted on each project depending on the application of the concrete. Even with all the current equipment available today, there is far too much concrete rejected because the slump is out of even these generous (loose) tolerances. This rejection rate show there is still a need to improve the process of mixing batches of concrete.

However, when using the currently available technology, the process of producing concrete at a consistent slump is all in the operator's skill. Therefore, one benefit and objective of the present invention is that it can automatically adjust the water needed to acquire a desired slump, and another benefit and objective of the present invention is that it aids or trains an operator how to accomplish similar results manually using a variety of settings, real-time displays and user interfaces.

Therefore, the present inventor has recognized a need in the art for an improved concrete batch mixing control system which indicates to an operator when a batch is properly mixed with greater consistency, accuracy and repeatability. Present day concrete producers with multiple mixers using currently available slump meters have a hard time duplicating the slump of designated a batch of concrete because of the many variables in equipment being used. All mixers because of design, size, power supply, wear, etc., produce a different output and is not a stable analog output. Most meters available today produce a different and unstable reading for a designated batch in different mixers. There is a further need in the art, recognized by the present inventor, to provide a training human machine interface (HMI) which allows the operator to observe, learn, and optimize the batch timing to eliminate mixing beyond the completion point, in order to maximize mixing production output without sacrificing concrete quality.

To these ends, embodiments of the present invention provide an improvement to slump meters which includes an ability to calibrate/correlate a slump meter that displays a common stable readout, such as a stabilized digital output, and which targets in the process of duplicating a designated batch of concrete to a designated common number (hereinafter referred to as Unique Target Number UTN which is unitless), consistency, or slump on multiple mixers. Further to these ends, embodiments of the present invention provide for automatic feeding of water into an actively mixing mixer to minimize the time required to accomplish completion of the batch, and to signal the operator when the batch is complete in a manner that instills confidence in the operator so as to modify the operator's behavioral preference to over-mix for an extended period of time.

The prototype of the improved slump meter is based upon the present inventor's Ultameter™ central-mix monitoring system which has been proven in use in central-mix systems. This improved slump meter was designed for a central-mix concrete plant monitors and records in real time all the functions of the mixer including the slump, feed, mix, dump, return times and the plant discharge sequencing, all of which can be monitored from any remote computer or cell phone. In that process of designing this central-mix slump meter, the present inventor developed processes to program all of the mixers of different types and sizes to read the same values to yield the same concrete load parameters, thereby allowing operators to reliably interpret the readings without having to take into account individual differences between different mixing equipment, locations, ages, etc. According to the present invention, the inventor's prior central-mix monitoring system is further improved by addition of an innovative the presently disclosed automatic water feeding process which, when coupled to an accurate real time slump meter such as but not limited to the improved slump meter of the incorporated patent application, minimizes mix production time, and optionally trains operators to understand the true ending of a mix cycle. It will be readily appreciated by those skilled in the relevant arts that various embodiments of the present invention can be utilized in both ready-mix and central-mix operations, although the several example embodiments may be disclosed with reference to one operation type or the other.

As such, at least one embodiment of the present invention includes providing certain improvements to the existing Ultameter™ mixing operation monitor system. It is, therefore, useful on both electric- and hydraulic-driven concrete mixers for ¼ cubic yard (yd$^3$) thru 15 yd$^3$ mixers, for all makes and models of concrete mixers. It displays a modified digital reading produced from an analog signal obtained from a concrete mixer. The modified digital reading is the result of averaging and a delay in the signal output. The reading produced is more stable and easier to interrupt by the operator. The result is the ability to duplicate the consistency or slump of multiple batches of concrete to a more precise measurement. It will be readily understood by those skilled in the relevant arts that the improvements according to the present invention may be equally well applied to other slump meters, either in analog or digital form, and that the disclosed example embodiment does not indicate a limitation regarding application of the present invention to other slump meters.

Improved Slump Meter Used in Some Embodiments of the Present Invention

The present invention brings these benefits to central-mix production environments. For example, an improved slump meter might be designed to read 150 when the mixing drum is empty idle, to read 350 when the mixing drum contains a 7 yd$^3$ load having a 3" slump, or to read 220 when the mixing drum contains a 4 yd$^3$ load having a 5" slump. Embodiments according to the present invention calibrate and correlate a slump meter that is connected to a concrete mixer that can display a digital reading of a similar batch of freshly mixed concrete, regardless of size, make, or model of the concrete mixers. A preferred embodiment uses a 3-digit Unique Target Number (UTN) to index each concrete batch to a table, preferably stored in a spreadsheet, to at least one associated initial peak motor value, as is described in the following paragraphs.

The general procedure to provide these improvements comprises:
  a. Produce a Unique Target Number (UTN) for each mixer when running and empty.
  b. 2000/Raw data=conversion factor
  c. Conversion factor×Raw Data=2000
  d. 2000×15=30000 for averaging and to stabilize the output reading
  e. 30000/75=400 the average and stable number
  f. Average and stabilized number refreshed on meter every 1.25 seconds
  g. 400−250=150=a UTN for an empty running mixer This UTN can be displayed in inches and fractions of an inch, or by a 3-digit number, whichever is preferred by the concrete producer. This UTN can then be used during subsequent production of concrete by a logical control process according to the present invention to effectively duplicate a batch concrete with the prescribed size of the batch and the slump requested.

This process containing the Batch ID and the new actual 3-digit UTN can be created by using information from the actual testing of the slump of various size batches, such as:

Size of Batch (in yd$^3$) @ Slump (in inches)=3-digit UTN
8 yd$^3$ @ 3" slump=? 3-digit UTN or
8 yd$^3$ @ ? Slump=350 3-digital UTN.

There are two reference points in establishing the prescribed slump of a batch of concrete being loaded in a mixing operation, one is at an idle speed of the mixer unit, and the other is at the real-time mixing speed of the mixing drum while mixing a batch of concrete. The process created can include one or both as UTN.

The system according to the present invention will display one or more of the following measurements and calculations:
  1. Actual live number created by the loaded mixer
  2. Enter Batch Id number (requested load size and slump)
  3. Idle Target number
  4. Mixing target number
  5. Log data Button
  6. Enter mixer number
  7. Enter ticket number The system according to the present invention will record one or more of the following measurements and calculations:
  1. Central Mix Plant Number
  2. Batch ID Number (load size and slump)
  3. Time loaded
  4. Mix Time
  5. Time when data logged
  6. Slump idle target number
  7. Actual Slump idle number when data logged
  8. Ticket number By using this process, the raw data from the hydraulic or electric motor is converted to a UTN, such as shown in Table 1:

TABLE 1

Example Motor Power (Amps or PSI) to Slump Correlation

| Example: | Empty | Empty Target # | Actual | | 8 yds | Idle Target # | Mixing Target # | Actual |
|---|---|---|---|---|---|---|---|---|
| Mixer A | 800 psi | 2000 | 150 | 0" Slump | Mixer A | 3000 | 350 | 425 | 3" Slump |
| Mixer B | 825 psi | 2000 | 150 | 0" Slump | Mixer B | 3000 | 350 | 425 | 3" Slump |
| Mixer C | 850 psi | 2000 | 150 | 0" Slump | Mixer C | 3000 | 350 | 425 | 3" Slump |

In this senereo the target # for each mixer to produce a 8 yd load with a 3" slump are all the same After the improved slump meter is calibrated for each installation on a particular mixer unit, the readings produced by the system according to the present invention will be the same (consistent) across all batches for all mixer units, regardless of the size, make, model age or condition of the mixing unit, as shown, for example, in Table 2:

TABLE 2

Example Motor Power (Amps or PSI) to Slump Correlation

| Example: | |
|---|---|
| Mixer A | 10 cubic yd Hydralic mixer = 800 psi = empty = 2000 = 150 and 8 cubic yds @ 350 = 3" slump |
| Miixer B | 15 cubic yd electric mixer = 50 amps = empty = 2000 = 150 and 8 cubic yds @ 350 = 3" slump |

Figure 10:
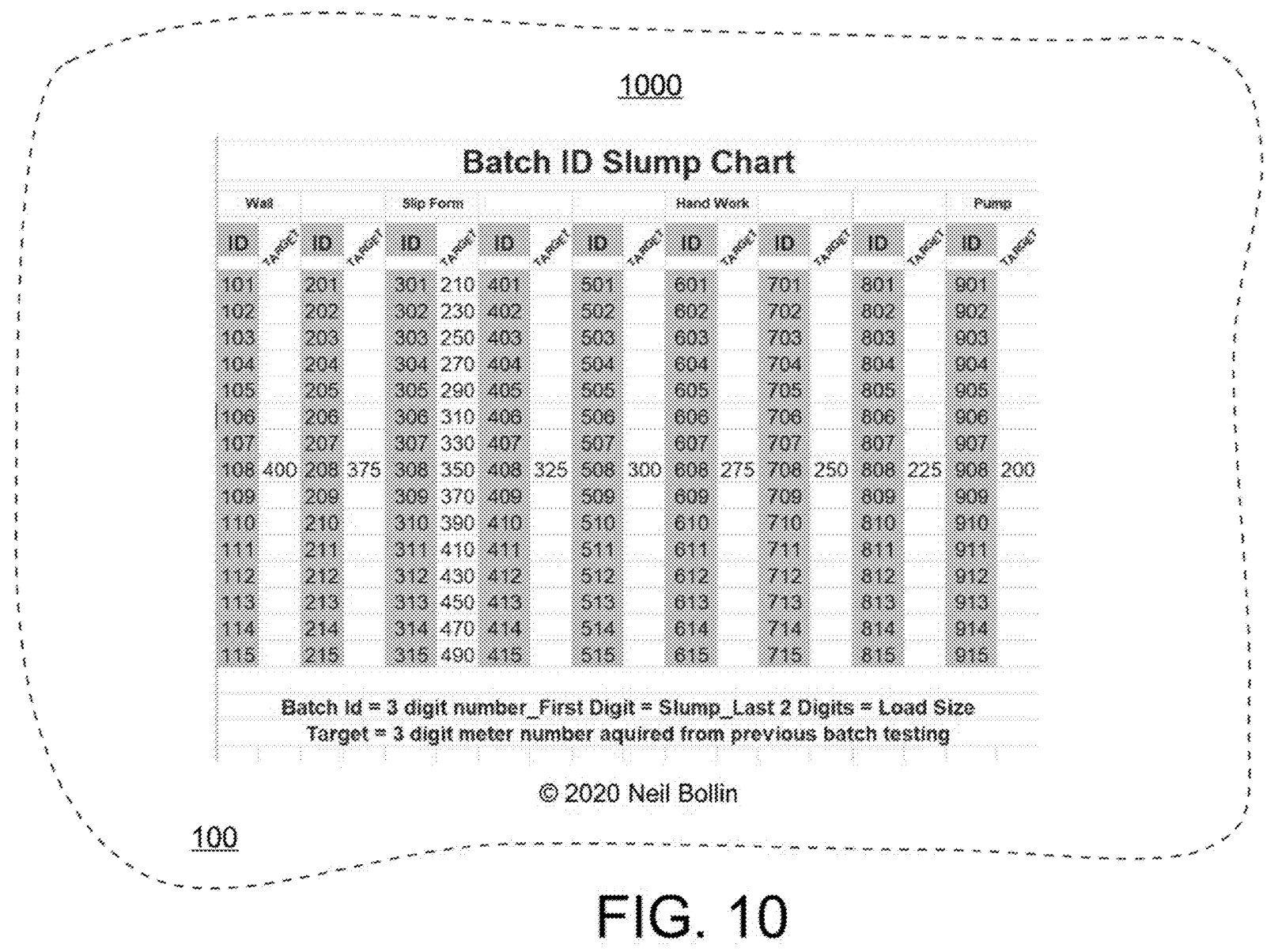
Figure 12:
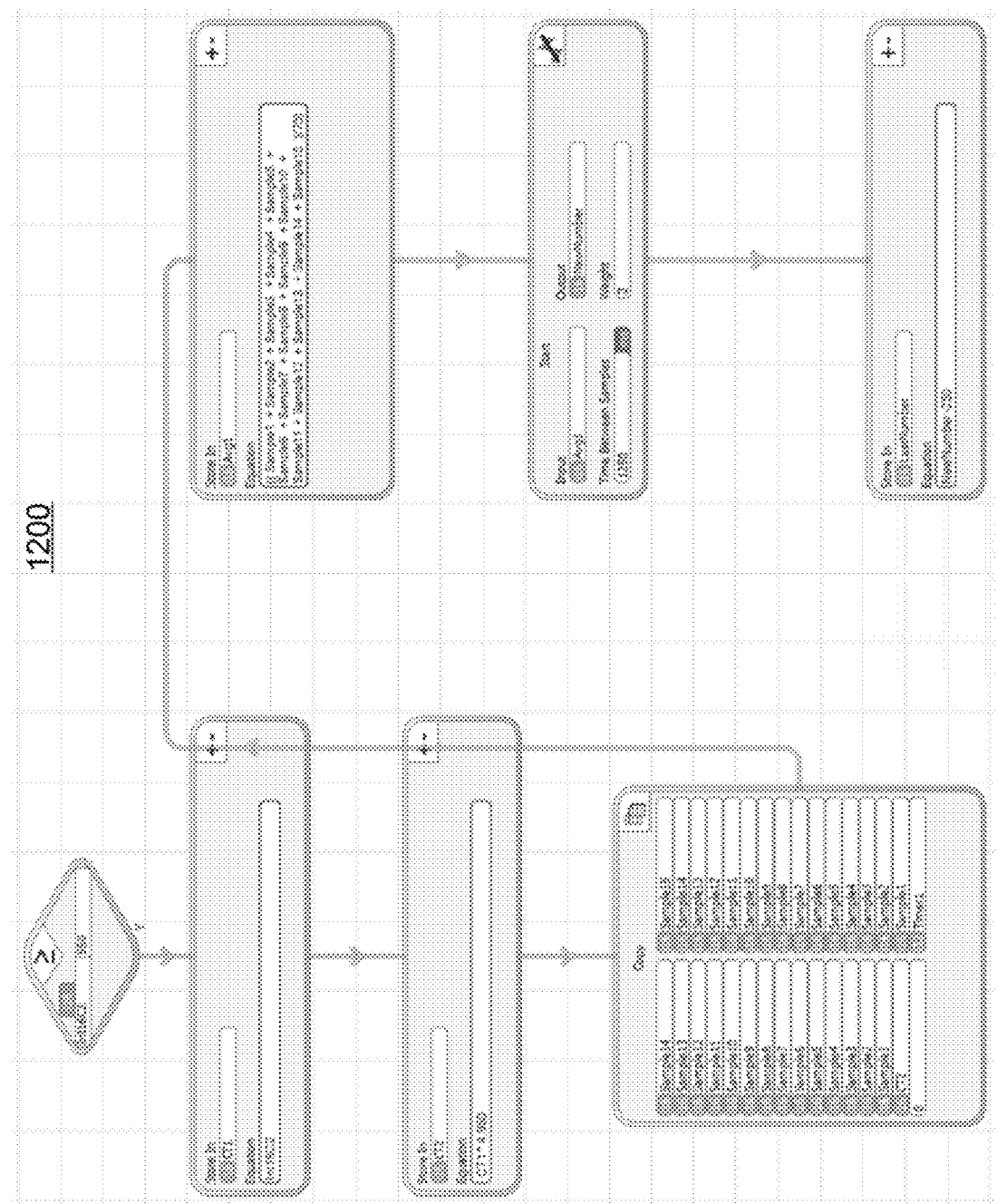
FIG. 12 illustrates a logical flow suitable for performance by a microprocessor according to at least one embodiment of the present invention.

As such, the processes, devices and systems according to the present invention can be produced for the multitude of mix configurations needed and therefore any mix consistency can be easily duplicated or created. An example slump chart 1000 according to the present invention is provided in FIG. 10. FIG. 12 provides a logical process flow 1200 suitable for performance by a microprocessor of an industrial controller, such as a Programmable Logic Controller, according to at least one embodiment of the present invention, to synchronize slump indicators to produce the same or similar slump meter readings for an identical batch of concrete (in cubic yards and slump target) in concrete mixers of various types, sizes and shapes.

Peak-Driven Control

Figure 14:
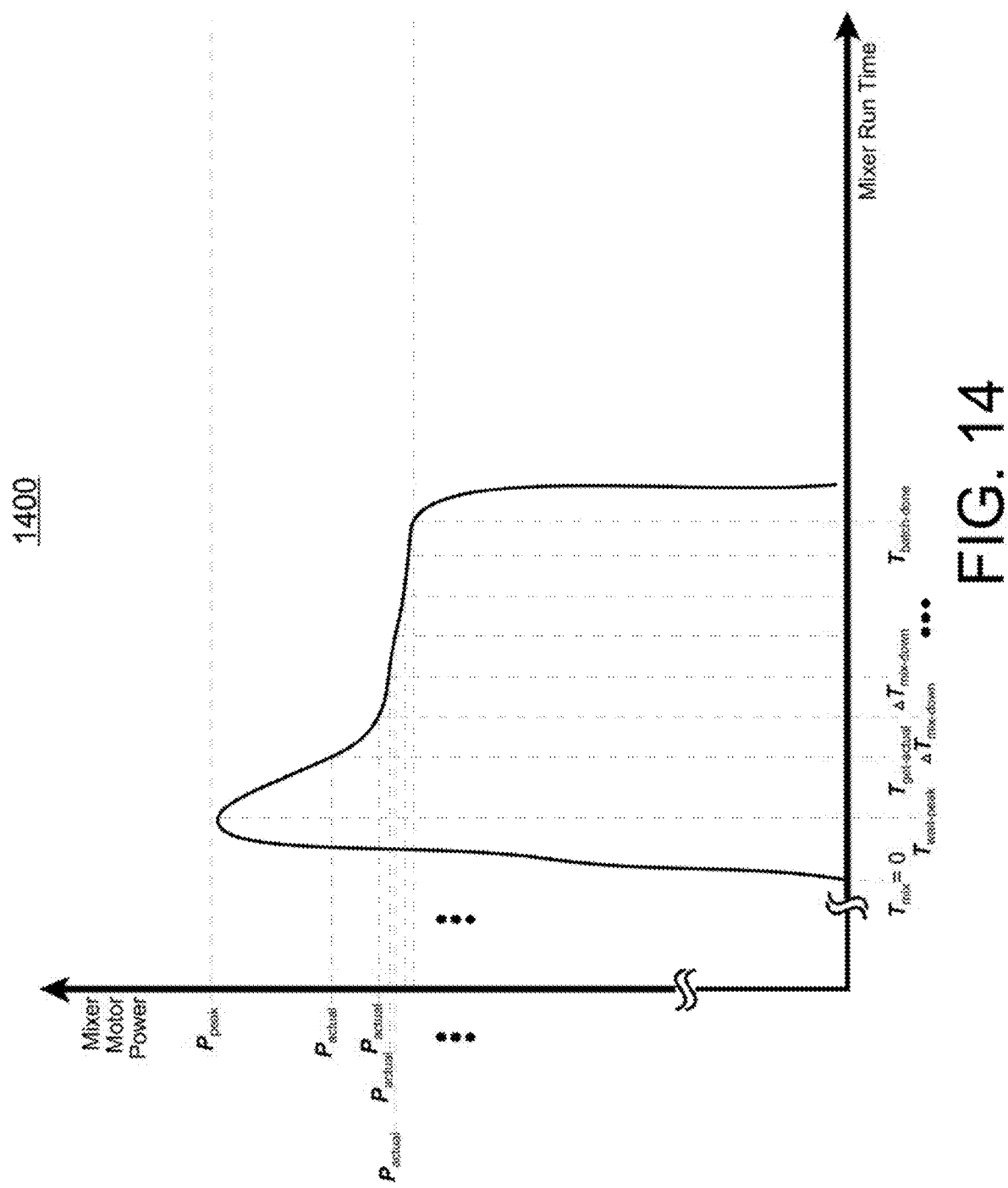
FIG. 14 provides an example mixer motor power plot over time according to the present invention.

The present inventor has discovered, tested and verified that mixer motor power exhibits a peak value upon initial feeding (loading) of the mixer with the batched components and water, as shown 1400 in FIG. 14. The peak mixer motor power $P_{peak}$ will typically be detectable in a reliable time $T_{wait-peak}$, such as 12 seconds for an example embodiment, after the mixing starts at $T_{mix}=0$. The present inventor has also discovered that, since the power curve is somewhat similar from one batch to another, a second sample of the mixer motor value at a pre-determined delay, such as at $T_{get-actual}=35$ seconds after $T_{mix}=0$, to confirm that the mixer motor power is decreasing normally due to the mixing of the batched components in the mixer. Thereafter, samples and small water adjustments on a repetitive periodic basis, such as $\Delta T_{mix-down}=10$ seconds, can be made to determine and add smaller amounts of water to bring the mixer motor power down reliably but quickly to the target power value, which corresponds to the target slump value of the batch.

Improvements to Concrete Mixer Control Systems

Embodiments of the present invention, which have been named by the inventor Ultameter Marc-I™, is an HMI/PLC device specifically developed for the concrete producer that wants to put the best tools available in front of their plant operator, which can improve both the quality and production quantity. The MARC system name is based on an acronym for the advanced system's main functions and benefits:

M: Monitor:
digital mixer reading,
real time charting of batch,
cycle time of batch, and
amount of temper water added.
A: Analyze:
batch cycle times,
hourly and daily production, and
final readings for consistency.
R: Record:
batch count,
date time of each batch,
batch cycle time, and
temper water added.
C: Control:
slump automatically or manually, and
production levels.

The Ultameter MARC™ is, in some embodiments according to the present invention, a stand-alone unit that can be adapted to any and all plant control systems A primary function of the Ultameter MARC™ is to aid and assist in obtaining the maximum production of quality freshly mixed concrete from central-mix concrete plant. All the data retained by the Ultameter MARC™ pertains only to the overall efficiency of the mixer and the plant it is connected to.

The Ultameter displays in real time and records the relevant data needed to improve the quality and production. All the data retained by the Ultameter pertains only to the overall efficiency of the plant and mixer it is connected to.

In some embodiments, the only information that is used from the batch ticket and plant control system is the batch size and slump target. Any and all other information of a batch that may be needed can be correlated by the date and time of the batch in the plant control system which is completely separate hardware.

Menu User Interface

Figure 4:
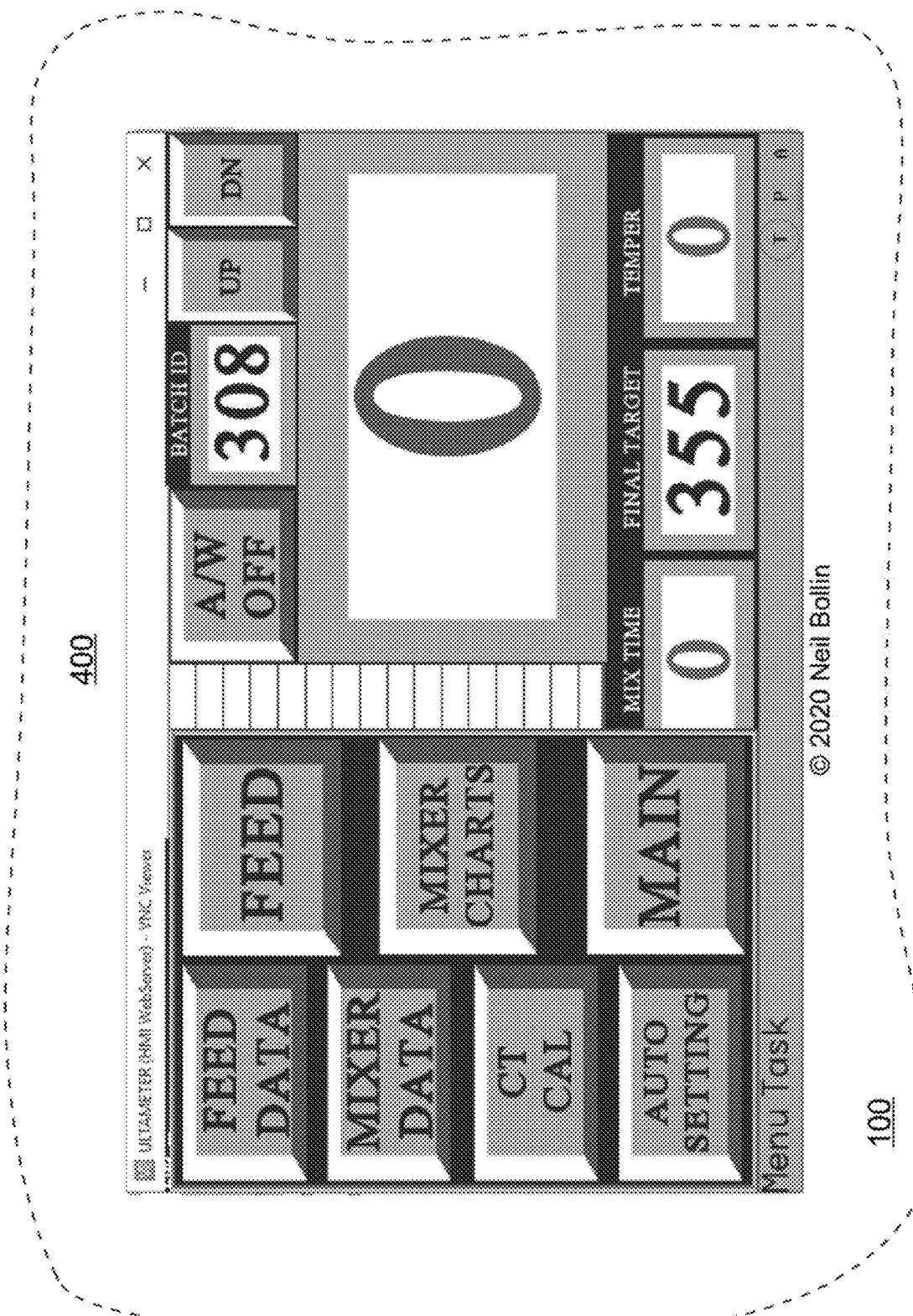
FIG. 4 illustrates an example user interface for a top-level menu according to at least one embodiment of the present invention.
Figure 11:
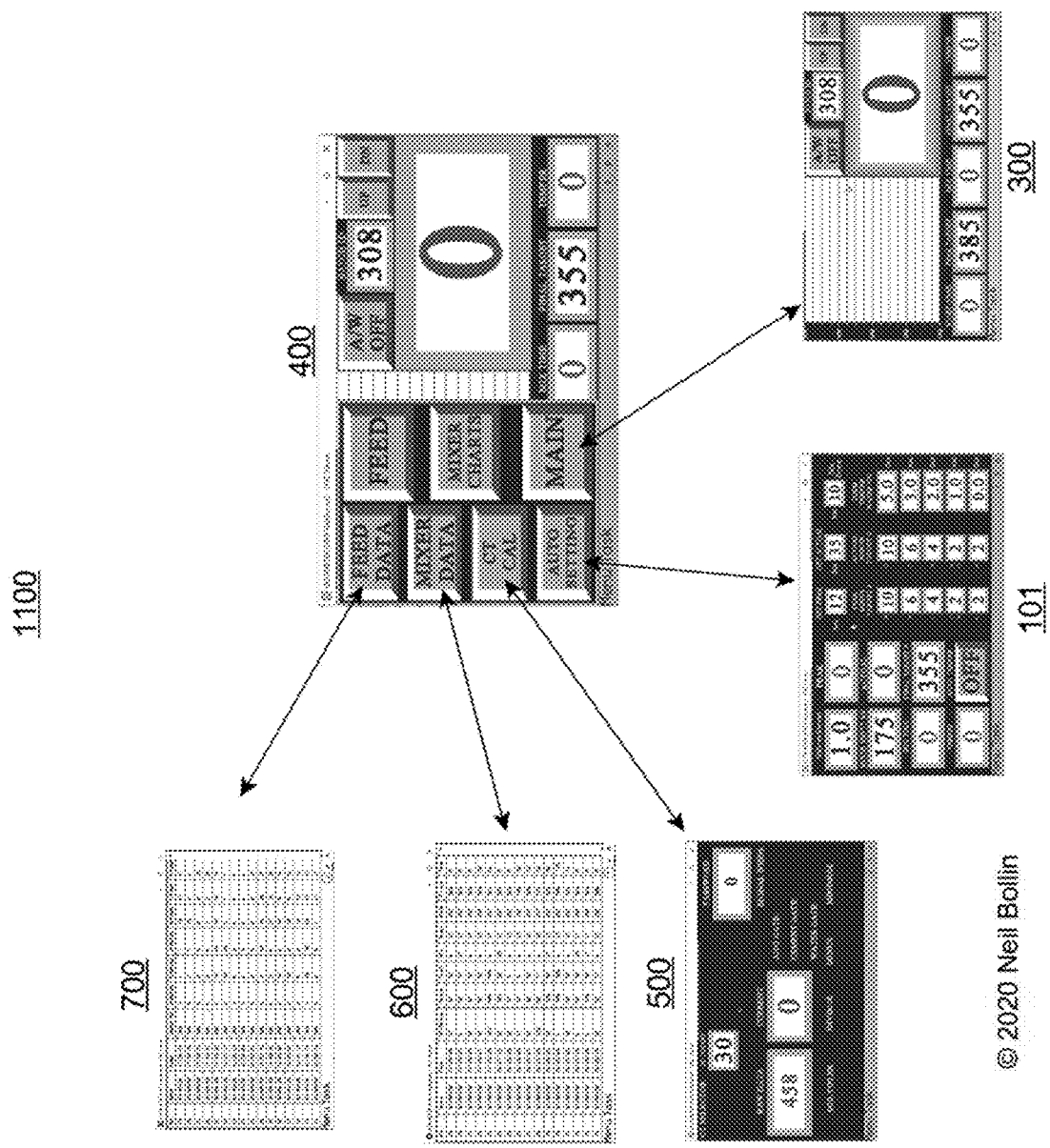
FIG. 11 illustrates an example organization of the various example user interfaces according to at least one embodiment of the present invention.

According to an example embodiment of the present invention, a top-level Menu user interface 400 is provided, such as that shown in FIG. 4, displayed on a portion 100 of a user interface device, such as a CRT, Plasma, LCD or LED computer screen, to allow the operator to navigate 1100 the other various user interfaces of the system as depicted in FIG. 11:

1. Main=Main Screen
2. Mixer Charts=Here are 2 charts that display the consistency and the Mix times of the last 20 batches.
3. Feed=This is the plant discharge sequencing of the last batch.
4. Feed Data=This is the database of the plant discharge sequencing, it also includes the Batch ID. This information is logged and accumulated as each batch is completed.
5. Mixer Data=This database is of all the mixer functions. This information is logged and accumulated as each batch is completed.
6. Target Data=This is where all the predetermined, Batch ID, Peak Target, and Final Target, information is entered and stored.
7. Auto Settings=This is where the Automatic Water Feed function is programmed. Also temper meter is calibrated and the mixer empty set point is entered.

Main Screen Operation

Figure 3A:
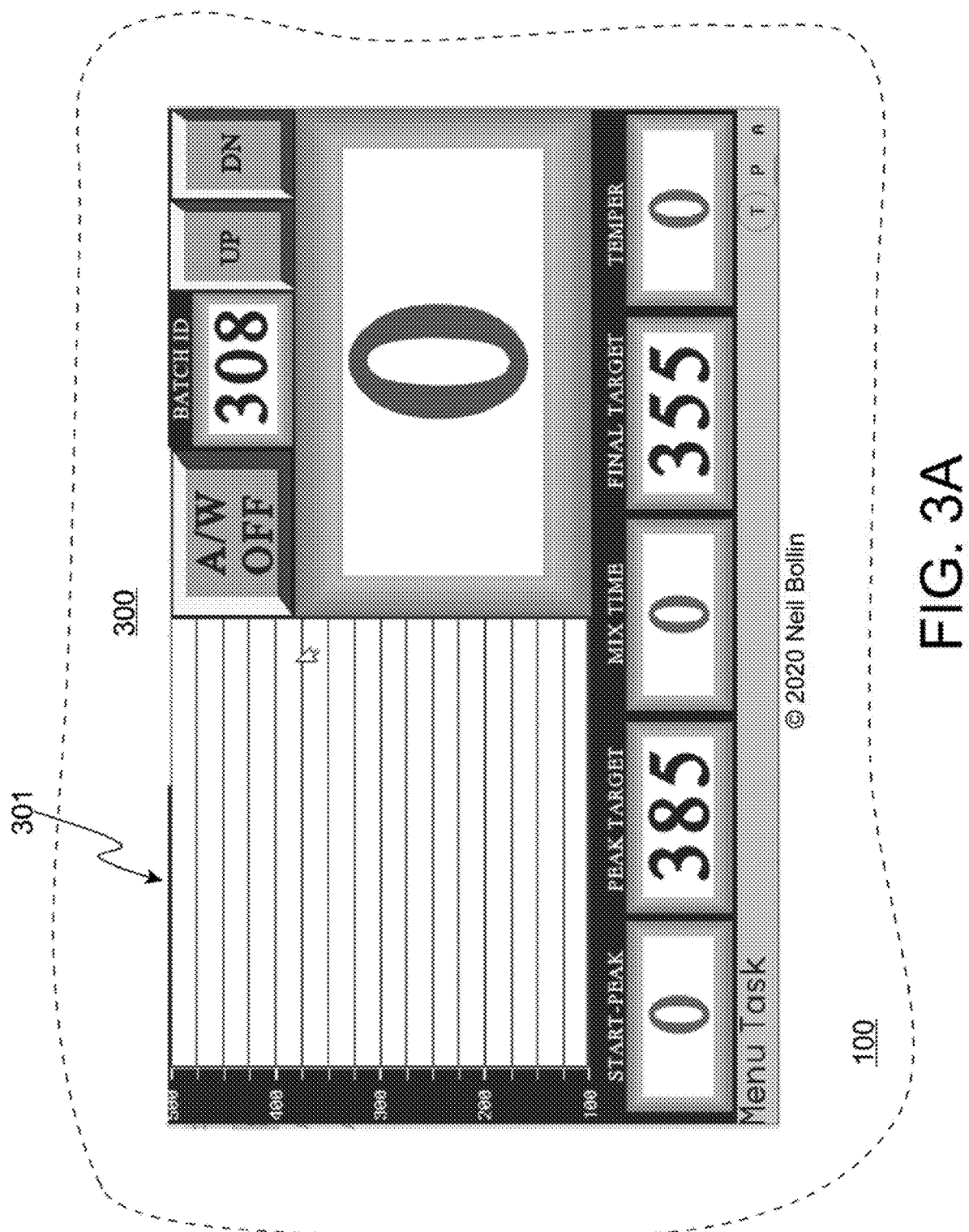
FIG. 3A illustrates an example user interface for a main display of central-mix mixing operations in real time according to at least one embodiment of the present invention.

Referring now to FIG. 3A, which depicts an example user interface for a central-mix Main Screen 300 for an exemplary Batch ID 308 (e.g., 3" slump, 8 yard batch) in which real time mixer motor power measurement is charted and graphed 301:

1. When the operator starts the plant discharge, the peak number (Start-Peak) flashes ON and the number increases until all the aggregate fed into in the mixer.
2. Pryor to the batch reaching the peak number, the feed gate closes and the Mix Time starts running a timer (in seconds).
3. The peak number that is displayed is the first indication of what the slump of the batch will be. Prior to this point of the batching, predetermined Batch ID and UTN values are entered into the Peak Target and Final Target and are the indications is added water is needed and when the mixer is ready to discharge, respectively.
4. At this point of the batching process a predetermined formula can be established for a particular batch of concrete. Peak Number+0 gallons of water(temper) =Final Target. These two numbers are entered and are used as a reference to how much temper water to add and when the mixer is ready to discharge.
5. If the peak number equals or is below the peak set point (Peak Target), in 30 seconds, with this particular example plant, the batch may be ready to dump as it will end up to be at or below the final set point and this would indicate a wet load.
6. If the peak number is above the peak set point, this would indicate a dry load and adjustments need to be started at this time, using data from previous batches.
7. The goal is to reach the final set point without going below and in the minimum amount of time allowed, this relies very heavily on the operator's skill in unimproved mixing control systems, but is automatically determined according to the present invention.
8. Ideally, in this example embodiment, the Water Trim needs to be set so the peak number locks in at about 8-10 gallon above the peak set point. This will compensate for the moisture changes that will occur.
9. When the Final Set Point is reached, the operator is prompted to Empty the Mixer without further delay or "over mixing" the batch.
10. When the mixer is empty the meter resets and is ready for the next batch to start.

Operational notes for the Main Screen Buttons are as follows:

Everything on this screen pertains to the mixer functions and is what the operator needs to monitor while Batching concrete.

The big number is a modified digital amp reading in real time.

The line graph beside it displays the batch as it is happening.

Start-Peak=this block populates when the plant discharge starts and increases till the peak is reached and retains that number until the batch is completed.

Peak Target=This is a predetermined number. If the actual peak number is higher, the batch will need water added. If it is lower, it indicates that the batch may be too wet and will need to be dumped as soon as possible.

Mix Time=This starts when all the material gates are closed and stops when the tilt or the dump button is pushed.

Final Target=This also is a predetermined number and when the actual number matches it, the batch is ready to dump.

Temper=the amount of extra water added.

A/W OFF=This is a toggle button and will turn the automatic water program on and off.

Batch Id=this is a 3 digit formula used to identify and select the predetermined settings for the current batch. The first digit is the slump number, the second and third digits are the batch size.

Enter p/f Target=Must be set to enter new targets.

Figure 3B:
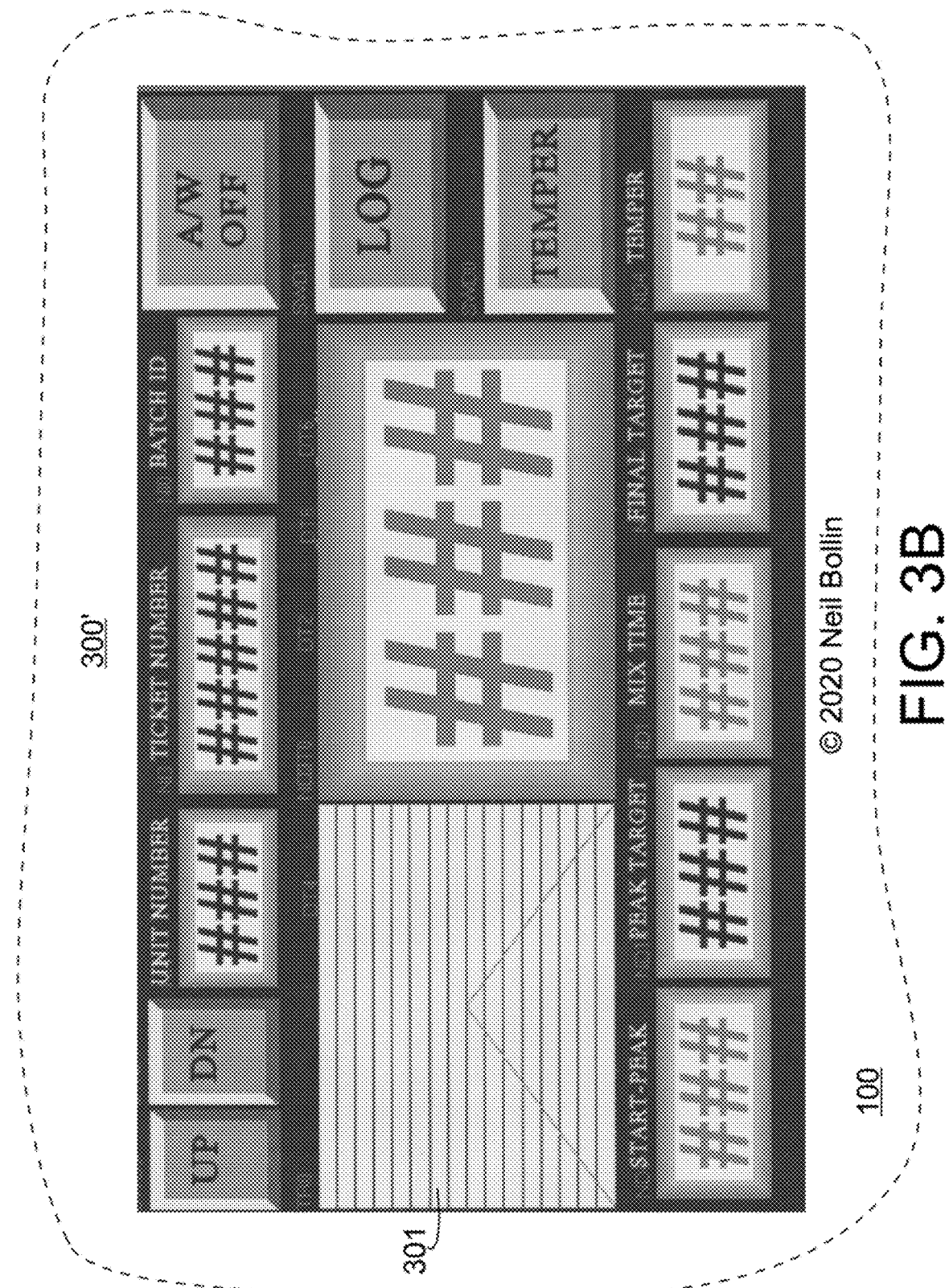
FIG. 3B illustrates an example user interface for a main display of ready-mix mixing operations in real time according to at least one embodiment of the present invention.

FIG. 3B depicts an example user interface for a ready-mix Main Screen 300', analogous to the main screen 300 shown in FIG. 3A for the central-mix operation, with appropriate differences.

Automatic Water Feed Control

According to the present invention, in addition to the user interfaces which allow the operator to adjust and calibrate the semi-automatic functions of the mixing control system, the operator is also equipped with an automatic water feed control function which injects the right amount of water, but not too much water, to achieve minimal bax mixing and production time.

Figure 2:
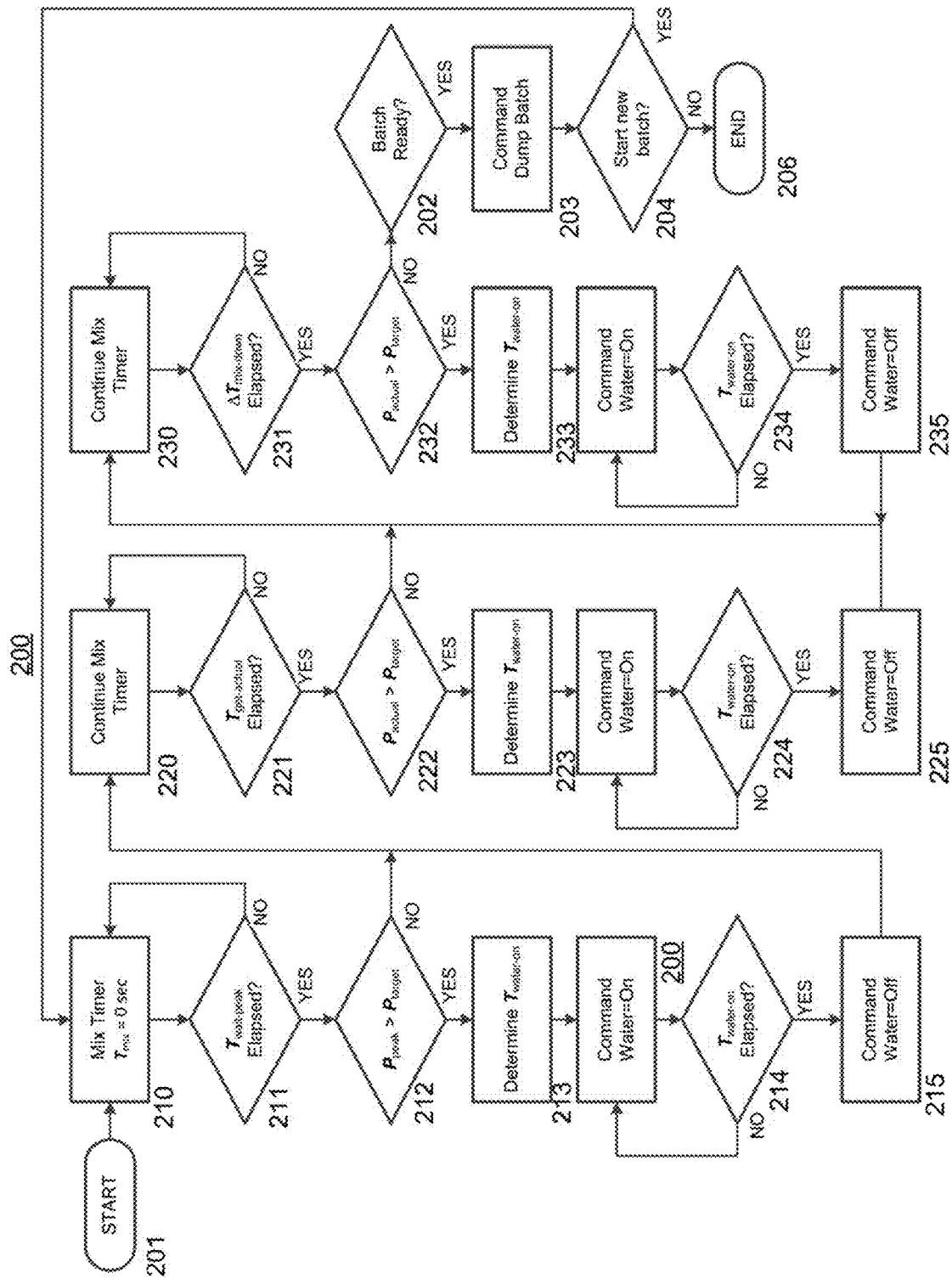
FIG. 2 illustrates a logical process suitable for performance by a microprocessor of a Programmable Logic Controller (PLC) according to at least one embodiment of the present invention.

FIG. 1 depicts an example user interface 101 to allow an operator to review, and if necessary, adjust the parameters 111, 112, and 113 of the automatic water feed process. FIG. 2 depicts an example logical process, suitable for execution by a microprocessor of an industrial control system, such as ladder logic for a PLC. The columns of parameters 111, 112, and 113 roughly correspond to the first three columns of steps 210-215, 220-225, and 230-235, respectively. When the process is started 201, the mix timer is cleared 210 to 0 seconds and started running. When the wait-for-peak time has elapsed 211, such as 12 seconds in the first column 111 of the UI, the peak value of the mixer motor power is measured. The difference between the peak value and the target value (batch is done value) is determine, and, in this example embodiment, the response to the difference is segmented into 5 ranges: greater than 10 over target, then automatically add water for 5.0 seconds; greater than 6 but less than 10 over target, then add water for 3.0 second; greater than 4 but less than 6 over target, then add water for 2.0 second; greater than 2 but less than 4 over target, then add water for 2.0 second; greater than or equal to 2 but less than or equal to 2 over target, then add water for 1.0 second; and less than 2 over target, then add water for 0.0 seconds. These values are adjustable by the user to customize and calibrate the automated steps 210-215 of the process.

Similarly, while the mix timer continues to elapse, a first actual mixer motor power value (after peaking) is measured and processed 220-225 according to the second column 111 of segmented responses. In this example, at 35 seconds of elapsed mixing time, water is automatically added to the mix according to the 5 ranges shown 111.

Similarly, after the second column of automatic water feed parameters 111 are processed once through, automatic water adding continues 230-235 in a repeating loop as controlled by the third column 113 of control parameters, such as every 10 seconds, until the final target motor power measurement has been reached, such as 355 in this example, which is detected as the batch being finished 202. When the system detects the batch is "ready" (finished), it either automatically commands the system to dump the batch from the mixer, or gives the operator a prompt to do so, or both. This minimizes the maximum time of mixing beyond the batch being ready to the value shown in the third column 113 of control parameters, such as 10 seconds, and therefore minimizes mixing time and maximizes production plant output by readying the mixer for the next batch within this time value (e.g., 10 seconds) of each previous batch being ready.

Through repetitious use of such an optimized, semi-automatic system, operators will overcome their learned behavior to "over mix" batches, waste mixing plant time, and to be more confident in dumping a batch earlier when it is actually ready. As such, the present invention serves both as an industrial control and a training system. Operators may learn, from observation, that the initial peak value of the mixing motor value is indicative of and correlates well to the amount of water to add to bring the mixture towards the target slump value as quickly as possible, rather than adding less water in the fear of making the batch too wet. While the automatic water feeding process automates this for the operator, the operator will learn from the process how to use the initial peak motor power value for future manual adjustments, as well.

Other User Interfaces

Figure 5:
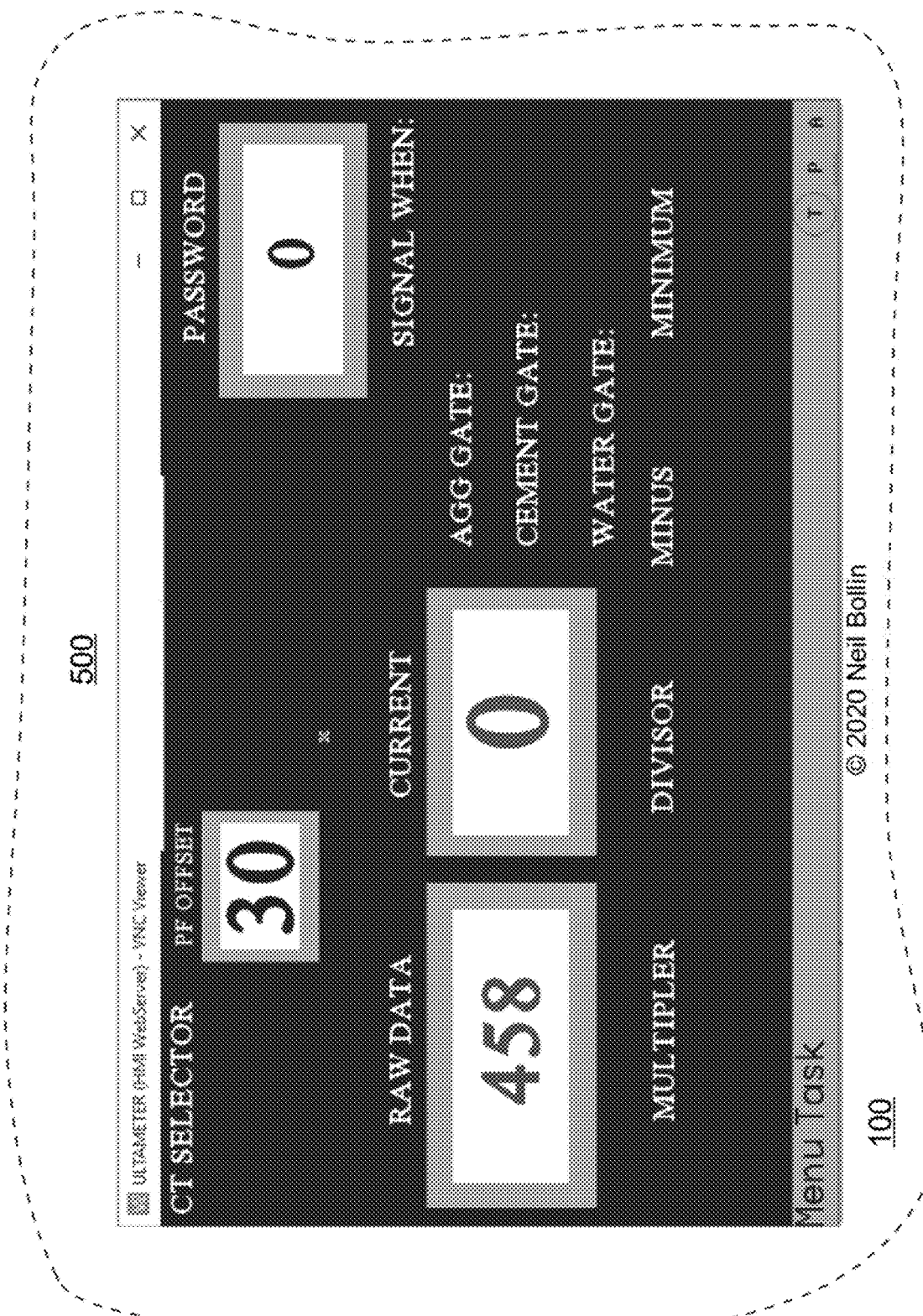
FIG. 5 illustrates an example user interface for system calibration according to at least one embodiment of the present invention.
Figure 7:
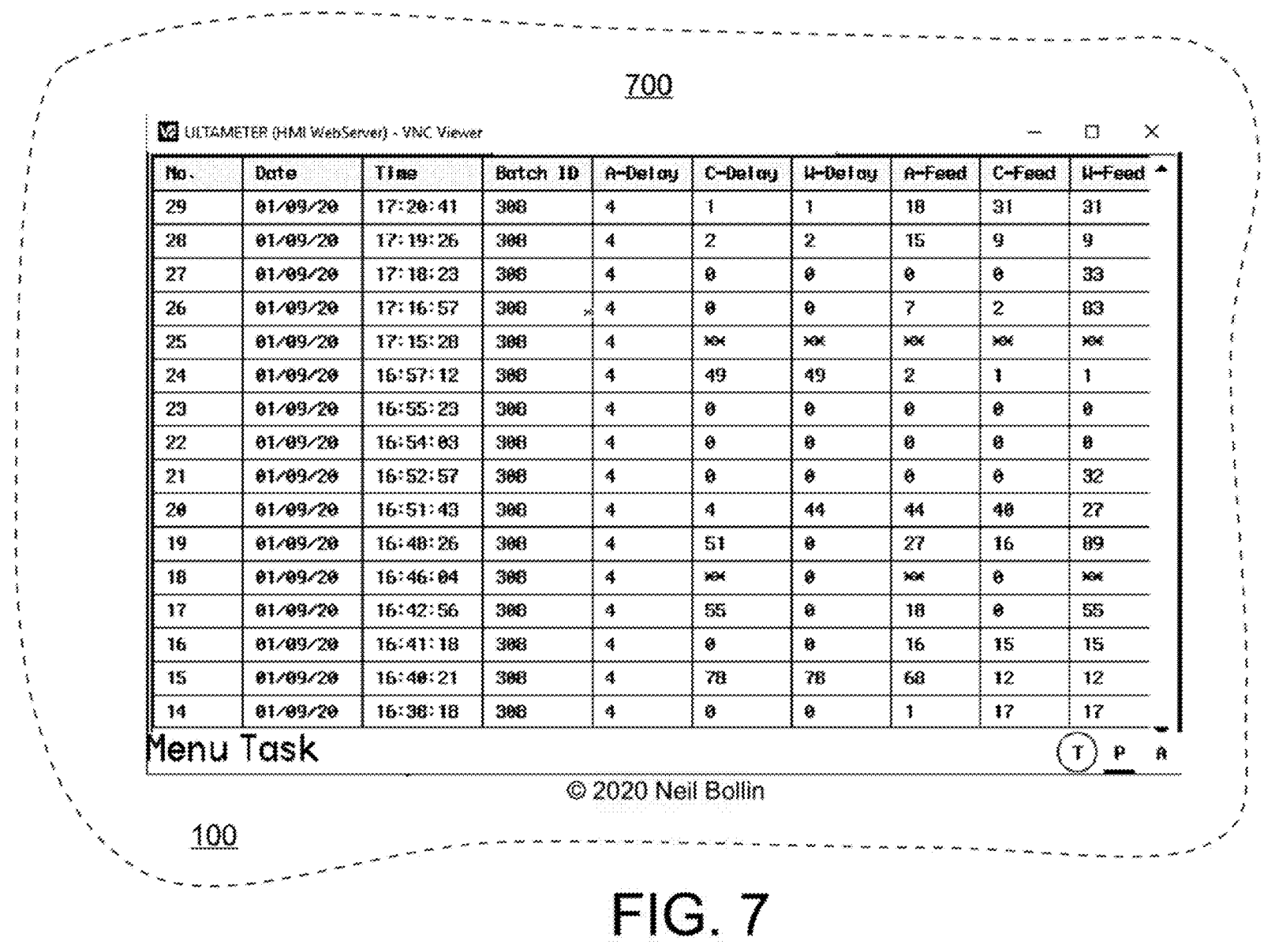
Figure 8:
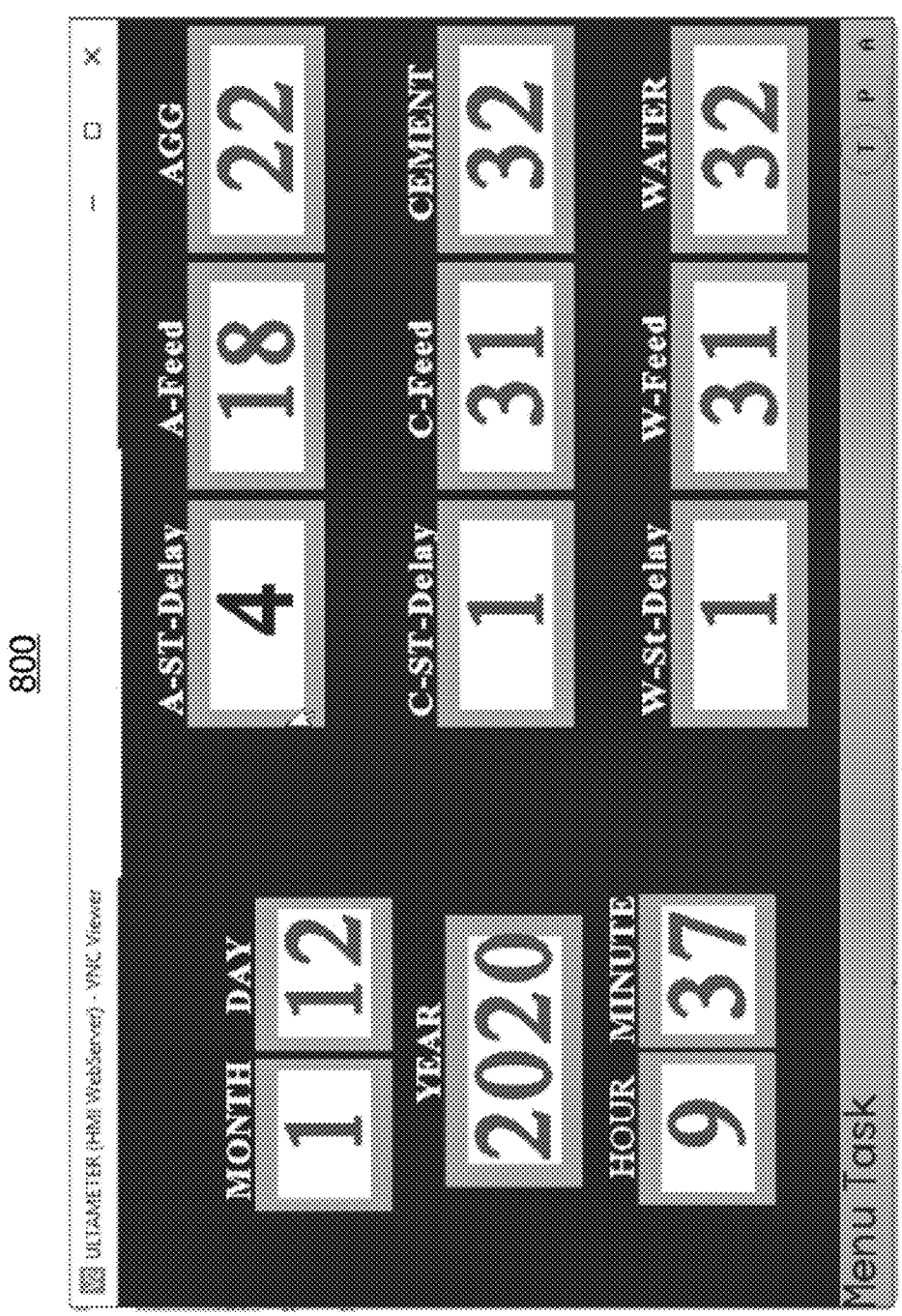
FIG. 8 illustrates an example user interface for reviewing the last production batch feed data according to at least one embodiment of the present invention.
Figure 9:
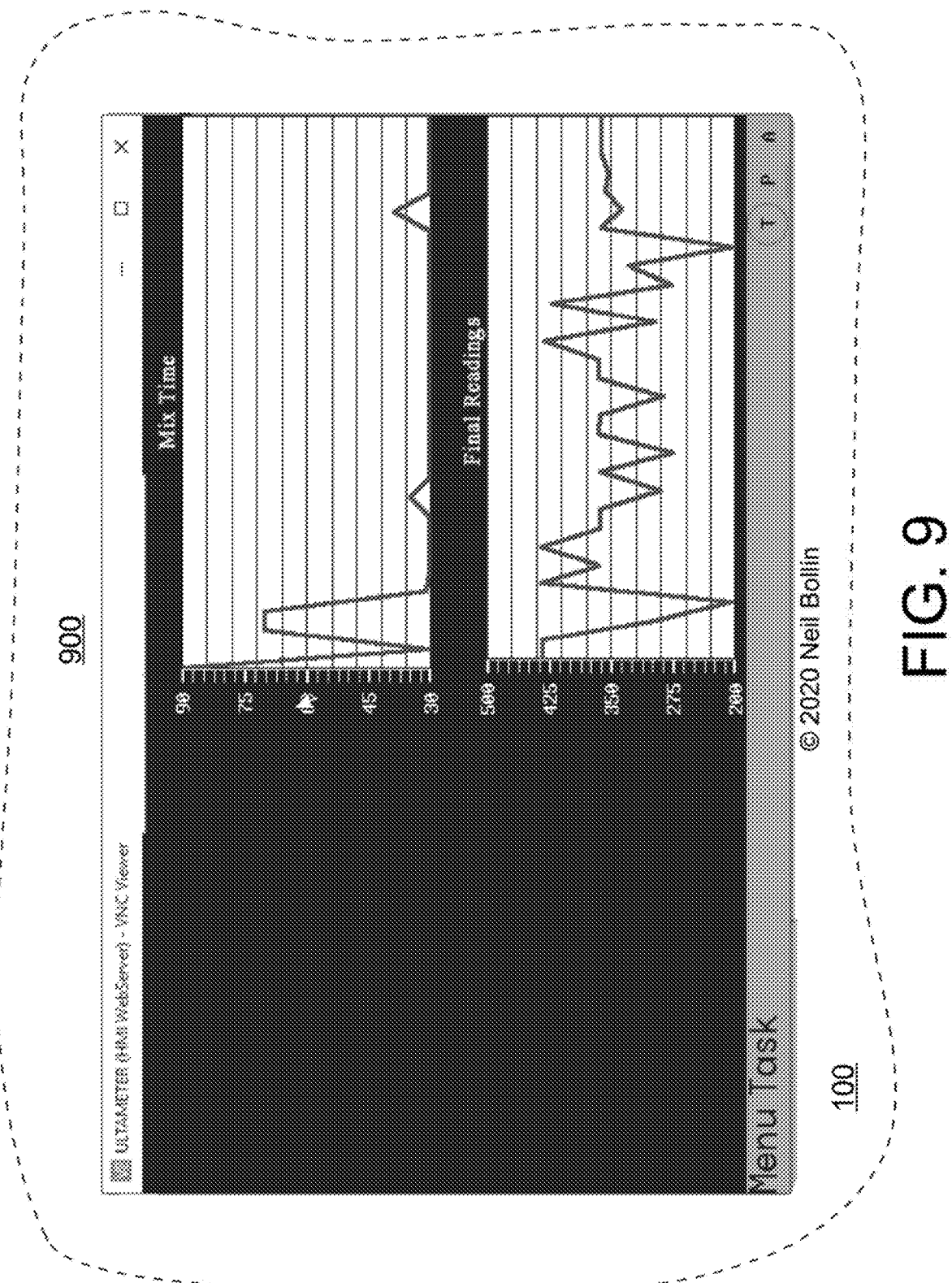
FIG. 9 illustrates an example user interface for reviewing a graphical representation (chart) of mix measurements of the most recent batches produced according to at least one embodiment of the present invention.

According to at least one embodiment of the present invention, several additional user interfaces are provided to the operator for additional reviewing and training purposes, and for additional control adjustment. FIG. 5 illustrates an example user interface for system calibration 500 according to at least one embodiment of the present invention. FIG. 6 illustrates an example user interface for reviewing and adjusting mixer data 600 according to at least one embodiment of the present invention. FIG. 7 illustrates an example user interface for reviewing and adjusting feed data 700 according to at least one embodiment of the present invention. FIG. 8 illustrates an example user interface for reviewing the last production batch feed data 800 according to at least one embodiment of the present invention. FIG. 9 illustrates an example user interface for reviewing a graphical representation (chart) of mix measurements 900 of the most recent batches produced according to at least one embodiment of the present invention.

Displayed and Recorded Information by Mixing Operation Type

Table 3 shows some of the information displayed by example embodiments of the invention when applied to a stationary (central-mix) or a mobile (ready-mix) concrete mixing operation.

TABLE 3

Example Information to be Displayed

| Information Item | Central-mix | Ready-mix |
| --- | --- | --- |
| Actual # | Yes | Yes |
| A/W Button | Yes | Yes |
| Batch ID Entry | Yes | Yes |
| Peak Target | Yes | Yes |
| Final Target | Yes | Yes |
| Mix Time | Yes | Yes |
| Water Added (temper) | Yes | Yes |
| Start-Peak | Yes | Yes |
| Up Button | Yes | Yes |
| Down Button | Yes | Yes |
| Actual Graph | Yes | Yes |
| Unit # Entry | No | Yes |
| Ticket # Entry | No | Yes |
| Temper Button | No | Yes |
| Log Button | No | Yes |

Table 4 shows some of the information which is recorded by example embodiments of the invention when applied to a stationary (central-mix) or a mobile (ready-mix) concrete mixing operation.

TABLE 4

Example Information to be Recorded

| Information Item | Central-mix | Ready-mix |
| --- | --- | --- |
| Date | Yes | Yes |
| Time | Yes | Yes |
| Batch ID | Yes | Yes |
| Peak # | Yes | Yes |
| Final # | Yes | Yes |
| Mix Time | Yes | Yes |
| Temper | Yes | Yes |
| Unit # | No | Yes |
| Ticket # | No | Yes |
| Feed Time | Yes | No |
| Dump (Discharge) Time | Yes | No |
| Start Delay | Yes | No |
| Cycle Time | Yes | No |
| Feed Sequencing | Yes | No |

System Architecture

Figure 13:
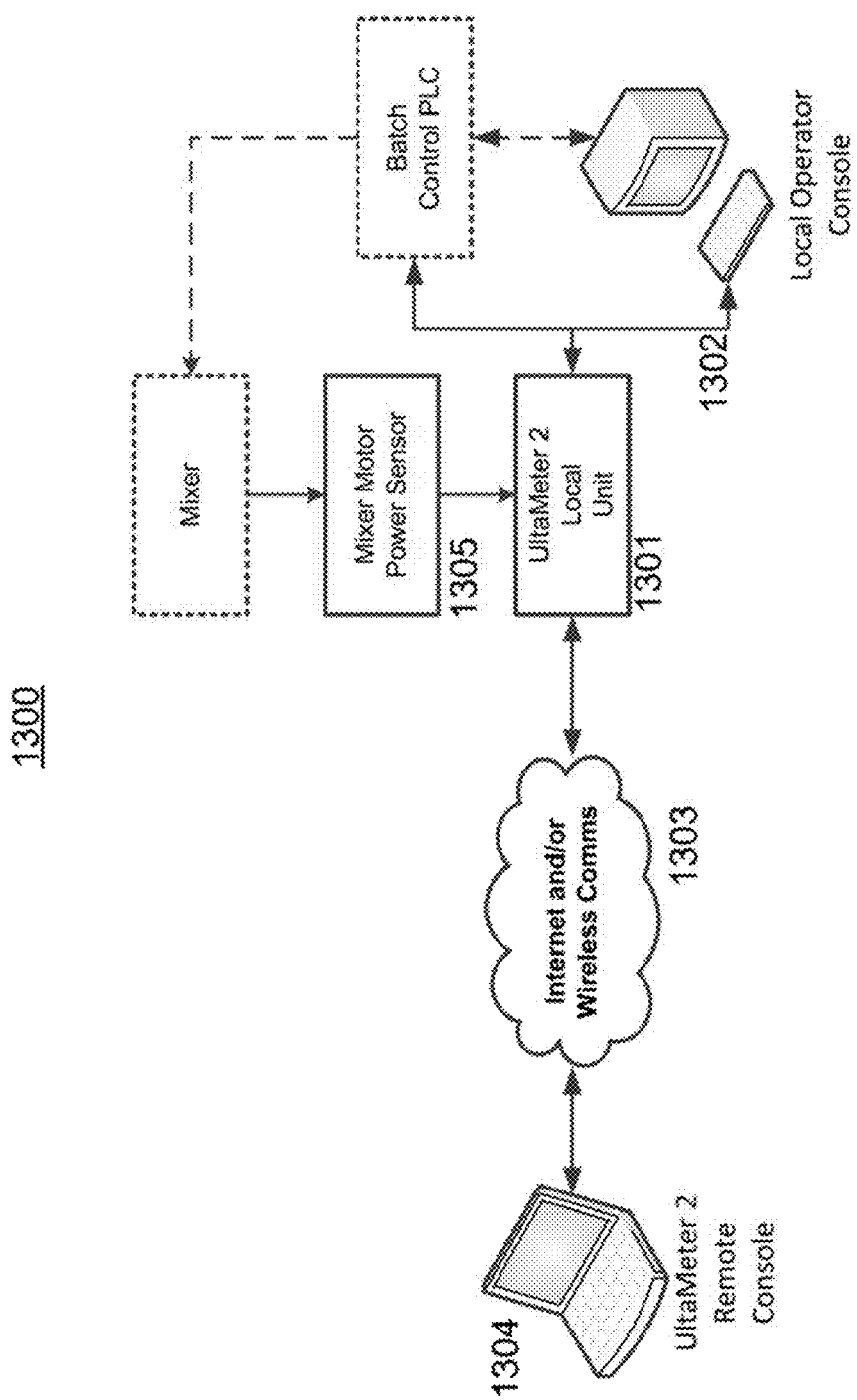
FIG. 13 depicts an example architecture of system components according to the present invention.

Referring now to FIG. 13, an example architecture 1300 according to the present invention is shown. A local unit 1301 is interfaced to a pre-existing mix control PLC 1302, and its display is used by the embodiment of the invention, such as for the user interfaces described in the foregoing paragraphs. A power sensor 1305 may be installed on the mixer motor and the local unit may interface to a computer network 1303, such as a local area network, a wireless network or the Internet. A remote console 1304, such as a table computer, smart phone or laptop computer, can then access some or all of the user interfaces remotely, and optionally, operate the mixing system controls remotely, as well.

Other architectures are available within the scope of the present invention, including integrating the foregoing processes and functions into an existing batch control PLC.

CONCLUSION

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof, unless specifically stated otherwise.

The corresponding structures, materials, acts, and equivalents of all means or steps plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

It will be readily recognized by those skilled in the art that the foregoing example embodiments do not define the extent or scope of the present invention, but instead are provided as illustrations of how to make and use at least one embodiment of the invention. The following claims define the extent and scope of at least one invention disclosed herein.

What is claimed is:

1. A method for automatically controlling concrete batch mixing cycles and for training an operator to minimize the mixing cycles, comprising the steps of:

responsive to introduction of water and dry materials for a batch of concrete into a mixer driven by a mixer motor, receiving, by a processor, a first time-related series of real time slump meter values, wherein the first time-related series of real time slump meter values begins synchronously with an introduction of water and dry materials without delaying for the water and dry materials to thoroughly mix together, wherein the real time slump meter values are received from a slump meter associated with a drum-turning motor from the mixer and wherein the real time slump meter values are approximately correlated to an expected slump value of a present state of contents of the mixer;

detecting, by a processor, an initial peak value among the first time-related series of real time slump meter values, wherein the initial peak represents an increasing trend up to the initial peak followed by a decreasing trend;

responsive to the detected initial peak value being above a pre-determined target slump meter value, determining, by a processor, a supplemental amount of water to add to the contents of the mixer of the batch of concrete;

waiting, by a processor, at least a first time period subsequent to the detecting of the initial peak value;

subsequent to expiration of the first time period and responsive to receiving by the processor a real time slump meter value in excess of the pre-determined target slump meter value, determining, by a processor, a next supplemental amount of water to contents of the mixer of the batch of concrete;

waiting, by a processor, at least a second time period after expiration of the first time period;

subsequent to expiration of the second time period and responsive to receiving by the processor an actual real time slump meter value in excess of the pre-determined target slump meter value, determining, by a processor, a next supplemental amount of water to add to the contents of the mixer of the batch of concrete; and subsequent to the determining of a second supplemental amount of water:
- monitoring, by the processor, one or more subsequently received real time slump meter values;
- detecting, by the processor, a real time slump meter value which meets the pre-determined target slump meter value; and
- activating, by the processor, an output signal for completion of the concrete batch.

2. The method as set forth in claim 1 wherein the steps of receiving comprise receiving at least one slump meter value generated from a real time mixer drum-turning motor selected from the group consisting of a hydraulic motor pressure measurement, an electric motor amperage measurement, and an electric motor wattmeter measurement.

3. The method as set forth in claim 1 wherein the steps of receiving further comprise retrieving, from a computer-memory stored spreadsheet file a pre-determined target slump meter value associated with a selected Batch ID value for a current concrete batch production, wherein the spreadsheet file comprises a plurality of pairs of Batch ID values and associated pre-determined target slump meter values.

4. The method as set forth in claim 1 further comprising providing, by a processor, a user interface configured to graphically illustrate to an operator the real time slump meter measurements.

5. The method as set forth in claim 1 further comprising providing, by a processor, a user interface configured to receive from an operator one or more settings from the group consisting of the pre-determined target slump meter value, a initial amount of water to add to a concrete batch, the first time period, and the second time period.

6. The method as set forth in claim 1 wherein the activating an output signal comprises activating one or more signals selected from the group comprising an indicator on a user interface to the operator of batch completion and a signal to a batch control system to automatically discharge the contents of the mixer.

7. The method as set forth in claim 1 further comprising the steps of:
- repeating, by a processor, waiting the second time period subsequent to the waiting after the first time period; and
- responsive to an actual real time slump meter value subsequent to the second time period exceeding the pre-determined target slump meter value, determining, by a processor, a next supplemental amount of water to add to the contents of the mixer of the batch of concrete.

8. The method as set forth in claim 1 wherein activating an output signal further comprises producing a water feed control signal.

9. The method as set forth in claim 8 wherein the water feed control signal comprises one or more signals selected from the group comprising an indicator on a user interface and a signal to a batch control system to automatically discharge the contents of the mixer.

* * * * *